United States Patent
Awad et al.

(10) Patent No.: US 11,617,719 B1
(45) Date of Patent: Apr. 4, 2023

(54) MORINGA OLEIFERA NANOPARTICLES

(71) Applicant: KING SAUD UNIVERSITY, Riyadh (SA)

(72) Inventors: Manal Ahmed Gasmelseed Awad, Riyadh (SA); Promy Virk, Riyadh (SA); Mai Abdelrahman Elobeid Wagealla, Riyadh (SA); Sarah Saleh Abdulla Alsaif, Riyah (SA); Awatif Ahmed Hendi, Riyadh (SA); Khalid Mustafa Osman Ortashi, Riyadh (SA); Rabia Qindeel, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 16/988,077

(22) Filed: Aug. 7, 2020

(51) Int. Cl.
*A61K 9/14* (2006.01)
*A61K 47/36* (2006.01)
*A61P 35/00* (2006.01)
*A61K 47/32* (2006.01)
*A61P 3/10* (2006.01)
*A61K 36/31* (2006.01)

(52) U.S. Cl.
CPC ............... *A61K 9/14* (2013.01); *A61K 36/31* (2013.01); *A61K 47/32* (2013.01); *A61K 47/36* (2013.01); *A61P 3/10* (2018.01); *A61P 35/00* (2018.01)

(58) Field of Classification Search
CPC .......... A61K 9/14; A61K 47/32; A61K 47/36; A61K 36/31; A61P 35/00; A61P 3/10
See application file for complete search history.

(56) References Cited

U.S. PATENT DOCUMENTS

| | | | |
|---|---|---|---|
| 9,789,146 B1* | 10/2017 | Awad | A61K 9/5161 |
| 10,442,618 B2 | 10/2019 | Sugiura et al. | |
| 2016/0243176 A1 | 8/2016 | Raskin et al. | |
| 2019/0209634 A1 | 7/2019 | Vieira | |

FOREIGN PATENT DOCUMENTS

IN     201741025589 A     7/2017

OTHER PUBLICATIONS

Al-Asmari et al., Moringa oleifera as an Anti-Cancer Agent against Breast and Colorectal Cancer Cell Lines, Aug. 19, 2015, PLOS ONE, pp. 2-14. (Year: 2015).*
Chowdary et al., Evaluation of Olibanum Resin as Microencapsulating Evaluation of Olibanum Resin as Microencapsulating Agent for Controlled Drug Delivery Agent for Controlled Drug Delivery, Aug. 2006, Indian Journal of Pharmaceutical Sciences, pp. 461-464. (Year: 2006).*
Abd-Rabou et al., "Moringa oleifera Root Induces Cancer Apoptosis more Effectively than Leave Nanocomposites and Its Free Counterpart," Asian Pacific Journal of Cancer Prevention, 18(8), 2017, pp. 2141-2149.
Vergara-Jimenez et al., "Bioactive Components in Moringa Oleifera Leaves Protect against Chronic Disease," Antioxidants, 6(4) 91, Nov. 16, 2017.
Tiloke et al., "Moringa oleifera and their phytonanoparticles: Potential antiproliferative agents against cancer." Biomedicine & Pharmacotherapy, 108 (2018), pp. 457-466.
Bhattacharya et al., "A Review of the Phytochemical and Pharmacological Characteristics of Moringa oleifera," Journal of Pharmacy and Bioallied Sciences, 10(4), Oct.-Dec. 2018, pp. 181-191.
Zare et al., "Antimicrobial gum bio-based nanocomposites and their industrial and biomedical applications," Chemical Communications, Issue 99, 2019, pp. 14871-14885.
Pandit et al, "Curcumin nanoparticles: physico-chemical fabrication and its in vitro efficacy against human pathogens," Biotech 3(5): pp. 991-997 (2015).
Shai, L. J. et al., "Inhibitory Effects of Five Medicinal Plants on Rat Alpha-Glucosidase: Comparison with their Effects on Yeast Alpha-Glucosidase," J. Med. Plant Res. 5: pp. 2863-2867 (2011).

* cited by examiner

Primary Examiner — Ali Soroush
(74) Attorney, Agent, or Firm — Nath, Goldberg & Meyer; Richard C. Litman

(57) ABSTRACT

The *Moringa oleifera* nanoparticles may be synthesized by harvesting *Moringa* leaves, drying the *Moringa* leaves, powdering the dried *Moringa* leaves, suspending the powdered *Moringa* leaves in a solution, and spraying the solution into boiling water under ultrasonic conditions to obtain *Moringa* nanoparticles. The *Moringa* nanoparticles may be encapsulated by dissolving the *Moringa* nanoparticles and gum olibanum in ethanol to produce a mixture, injecting the inert organic phase of the mixture into an aqueous solution containing PVA, and homogenizing the aqueous solution. The *Moringa* nanoparticles may be useful in preventing the growth of cancer cells and in treating diabetes by inhibiting α-glucosidase and/or α-amylase activity.

3 Claims, 8 Drawing Sheets

MORINGA OLEIFERA NANOPARTICLES

BACKGROUND

1. Field

The disclosure of the present patent application relates to nanotechnology, and particularly to *Moringa oleifera* nanoparticles, methods of synthesizing *Moringa oleifera* nanoparticles, and to methods of administering *Moringa oleifera* nanoparticles to inhibit the growth of cancer cells.

2. Description of the Related Art

Recently, nanoparticles have demonstrated important uses in a variety of fields. Nanoparticles have been used in a vast array of applications, including electronics, sensing, optics, and medicine.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. Encapsulation of nanoparticles with synthetic or bio polymers ensures more stability and controlled delivery, hence improving the bioavailable status of some nano-formulations. These methods are often costly or produce by-products that pose increased risks to human health and the environment.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used.

*Moringa oleifera* Lam. is commonly known as the drumstick tree of the Moringaceae family. It is a native of India and currently grown widely in many tropical and subtropical countries (Mbikay, 2012). Traditionally, *Moringa oleifera* is considered to be one of the most therapeutically useful trees, as almost all the parts (pods, leaves, flowers, roots and bark) have been reported to have a gamut of medicinal and nutritional properties (Singh et al., 2014). *Moringa* leaves are a good source of natural antioxidant due to the presence of various types of antioxidant compounds such as ascorbic acid, flavonoids, phenolics and carotenoids (Anwar et al., 2005; Makkar and Becker, 1996; Mbikay, 2012). These bioactive compounds are thought to be found in *Moringa* leaves and have been widely used in various studies as wound healing, anti-tumor, anti-fertility, hypotensive, antipyretic, antihepatotoxic, antiepileptic, anti-inflammatory, antiulcer, diuretic hypocholesterolemic, antifungal, antibacterial and anti-cardiovascular and anti-diabetic agents (Hussain et al., 2014; Jung, 2014).

Due to the pharmacological properties and rich nutritional value of the *Moringa* leaves, there has been a growing interest in promoting it as a food supplement or nutraceutical in the human diet.

Thus, *Moringa oleifera* nanoparticles solving the aforementioned problems are desired.

SUMMARY

The *Moringa oleifera* nanoparticles may be synthesized by harvesting *Moringa* leaves, drying the *Moringa* leaves, powdering the dried *Moringa* leaves, suspending the powdered *Moringa* leaves in a solution, and spraying the solution into boiling water under ultrasonic conditions to obtain *Moringa* nanoparticles. In an embodiment, the *Moringa oleifera* leaves may be harvested from *Moringa oleifera* trees grown in Riyadh, Saudi Arabia. In an embodiment the powdered *Moringa* leaves may be suspended in an appropriate solvent, including but not limited to methanol.

In an embodiment, encapsulated *Moringa oleifera* nanoparticles may be synthesized by harvesting *Moringa* leaves, drying the *Moringa* leaves, powdering the dried *Moringa* leaves, suspending the powdered *Moringa* leaves in a solution, spraying the solution into boiling water under ultrasonic conditions to obtain *Moringa* nanoparticles, dissolving the *Moringa* nanoparticles and gum olibanum in ethanol to produce a mixture, injecting the inert organic phase of the mixture into an aqueous solution containing polyvinyl alcohol (PVA), and homogenizing the aqueous solution. In an embodiment, the *Moringa oleifera* leaves may be harvested from *Moringa oleifera* trees grown in Riyadh, Saudi Arabia. In an embodiment the powdered *Moringa* leaves may be suspended in an appropriate solvent, including but not limited to methanol. In an embodiment, the ratio of *Moringa* nanoparticles:gum olibanum:PVA may be 1:5:7 (w/w/w).

An embodiment of the present subject matter is directed to a pharmaceutical composition including the *Moringa* nanoparticles and a pharmaceutically acceptable carrier.

An embodiment of the present subject matter is directed to a method of making a pharmaceutical composition including mixing the *Moringa* nanoparticles under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of inhibiting cancer cell growth, including administering to a subject in need thereof a therapeutically effective amount of a pharmaceutical composition according to the present subject matter.

An embodiment of the present subject matter is directed to a method of treating diabetes, including administering to a subject in need thereof a therapeutically effective amount of a pharmaceutical composition according to the present subject matter.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
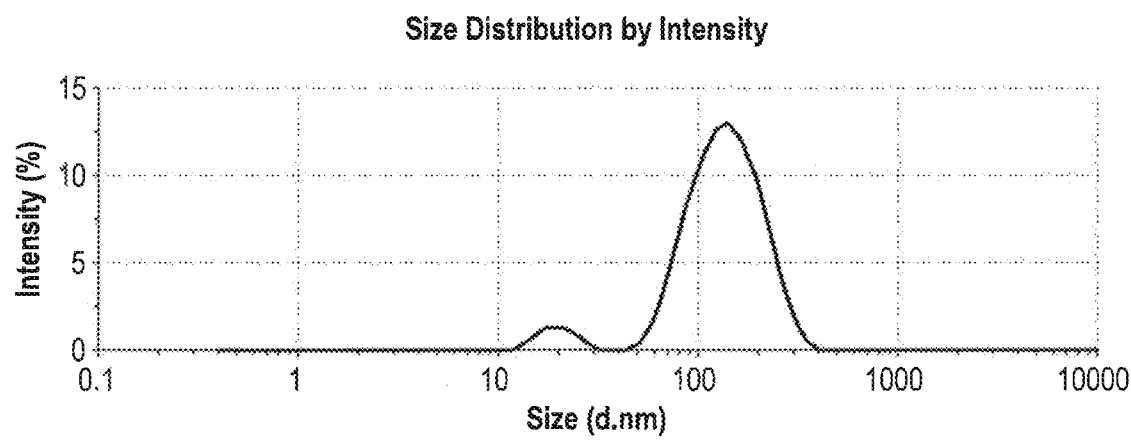
FIG. 1 depicts a Zetasizer spectrum of *Moringa oleifera* nanoparticles.

The *Moringa oleifera* nanoparticles may be synthesized by harvesting *Moringa* leaves, drying the *Moringa* leaves, powdering the dried *Moringa* leaves, suspending the powdered *Moringa* leaves in a solution, and spraying the solution into boiling water under ultrasonic conditions to obtain *Moringa* nanoparticles. In an embodiment, the *Moringa oleifera* leaves may be harvested from *Moringa oleifera* trees grown in Riyadh, Saudi Arabia. In an embodiment the powdered *Moringa* leaves may be suspended in an appropriate solvent, including but not limited to methanol.

In an embodiment, encapsulated *Moringa oleifera* nanoparticles may be synthesized by harvesting *Moringa* leaves, drying the *Moringa* leaves, powdering the dried *Moringa* leaves, suspending the powdered *Moringa* leaves in a solution, spraying the solution into boiling water under ultrasonic conditions to obtain *Moringa* nanoparticles, dissolving the *Moringa* nanoparticles and gum olibanum in ethanol to produce a mixture, injecting the inert organic phase of the mixture into an aqueous solution containing PVA, and homogenizing the aqueous solution. In an embodiment, the *Moringa oleifera* leaves may be harvested from *Moringa oleifera* trees grown in Riyadh, Saudi Arabia. In an embodiment the powdered *Moringa* leaves may be suspended in an appropriate solvent, including but not limited to methanol. In an embodiment, the ratio of *Moringa* nanoparticles:gum olibanum:PVA may be 1:5:7 (w/w/w).

In an embodiment, the synthesis of *Moringa* nanoparticles may include mixing about 400 mg of powdered *Moringa oleifera* leaves with about 20 ml of methanol and spraying the resulting solution into about 50 ml of boiling water dropwise at a flow rate of about 0.2 ml/min for about 5 minutes under ultrasonic conditions (ultrasonic power of 750 W and frequency of 20 kHz). The resulting solution may then be stirred at about 200-800 rpm at room temperature for about 20 minutes to produce the *Moringa* nanoparticles.

The *Moringa oleifera* leaves may be powdered by any available means of rendering a dried leaf into a powder, including but not limited to grinding, blending, and other similar techniques known in the art.

In an embodiment, the synthesis of encapsulated *Moringa* nanoparticles may include mixing about 150 mg *Moringa* nanoparticles with about 750 mg of gum olibanum and about 30 ml of ethanol to form a mixture, injecting the inert organic phase of the mixture into about 150 ml of an aqueous solution containing about 1,050 mg PVA, and homogenizing the resulting solution at about 22,000 rpm for about 25 minutes.

In an embodiment, the *Moringa* nanoparticles may have an average particle diameter of about 141.6 nm with a polydispersity of about 0.32.

In an embodiment, the encapsulated *Moringa* nanoparticles may have an average particle diameter of about 222 nm with a polydispersity of about 0.2.

As used herein, the term "about," when used to modify a numerical value, means within ten percent of that numerical value.

An embodiment of the present subject matter is directed to a pharmaceutical composition comprising the *Moringa* nanoparticles and a pharmaceutically acceptable carrier.

An embodiment of the present subject matter is directed to a method of making a pharmaceutical composition including mixing the *Moringa* nanoparticles with a pharmaceutically acceptable carrier. For example, the method of making a pharmaceutical composition can include mixing the *Moringa* nanoparticles under sterile conditions with a pharmaceutically acceptable carrier with preservatives, buffers, and/or propellants to create the pharmaceutical composition.

An embodiment of the present subject matter is directed to a pharmaceutical composition including the *Moringa* nanoparticles. To prepare the pharmaceutical composition, the *Moringa* nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The *Moringa* nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the *Moringa* nanoparticles or an amount effective to treat a disease, such as a bacterial infection, may be determined initially from the Examples described herein and adjusted for specific targeted diseases using routine methods.

The *Moringa* nanoparticles can be administered to a subject in need thereof. In an embodiment, the *Moringa* nanoparticles can be administered to a subject in need thereof to inhibit cancer cell growth and/or prevent or treat a cancer. In a further non-limiting embodiment, the cancer can be a breast cancer or a liver cancer. In a further embodiment, the *Moringa* nanoparticles can be administered to a subject in need thereof to treat the effects of diabetes. In a further non-limiting embodiment, the *Moringa* nanoparticles can be administered to a subject in need thereof in order to inhibit the activity of at least one of α-glucosidase, α-amylase, and a combination thereof.

An embodiment of the present subject matter is directed to a method of preventing cancer cell growth, comprising administering to a subject in need thereof a therapeutically effective amount of the pharmaceutical composition according to the present subject matter.

An embodiment of the present subject matter is directed to a method of inhibiting α-amylase activity, comprising administering to a subject in need thereof a therapeutically effective amount of the pharmaceutical composition according to the present subject matter.

An embodiment of the present subject matter is directed to a method of inhibiting α-glucosidase activity, comprising administering to a subject in need thereof a therapeutically effective amount of the pharmaceutical composition according to the present subject matter.

The *Moringa* nanoparticles or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The following examples illustrate the present subject matter.

Example 1

Synthesis of *Moringa oleifera* Nanoparticles

Fresh *Moringa* leaves were collected from *Moringa oleifera* trees grown in Riyadh, Saudi Arabia. The leaves were air dried and powdered to form powdered *Moringa oleifera* leaves. 400 mg of the powdered *Moringa oleifera* leaves was added to 20 ml of methanol, and the resulting solution was sprayed into 50 ml of boiling water dropwise at a flow rate of 0.2 ml/min for 5 minutes under ultrasonic conditions (ultrasonic power of 750 W and frequency of 20 kHz). The contents were then stirred at 200-800 rpm at room temperature for about 20 minutes.

Example 2

Synthesis of Encapsulated *Moringa oleifera* Nanoparticles

Encapsulated *Moringa oleifera* nanoparticles were synthesized using a ratio of *Moringa* nanoparticles:gum olibanum:PVA of 1:5:7 (w/w/w) using the nano precipitation technique as previously described (Bilati et al., 2005; Zili et al., 2005). Briefly, 150 mg of *Moringa oleifera* nanoparticles prepared according to Example 1 and an appropriate amount of olibanum were dissolved in 30 ml of ethanol. The internal organic phase of the resulting solution was then injected into 150 ml of an external aqueous solution containing the appropriate amount of PVA, and the solutions were homogenized at 22,000 rpm for 25 minutes.

Example 3

Characterization of *Moringa oleifera* Nanoparticles

Figure 2:
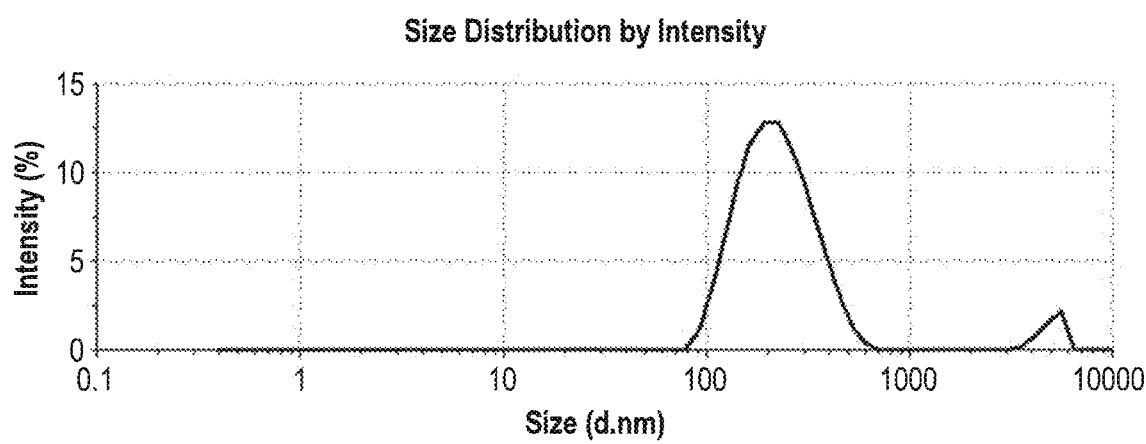
FIG. 2 depicts a Zetasizer spectrum of encapsulated *Moringa oleifera* nanoparticles.

Dynamic light scattering (DLS) analysis on a Zetasizer (ZEN 3600, Malvern, United Kingdom) was used to observe physical characteristics of the *Moringa* nanoparticles and the encapsulated *Moringa* nanoparticles. As shown in FIG. 1 and Table 1, the *Moringa* nanoparticles had an average diameter of 141.6 nm with a polydispersity of 0.32 and diverse sizes. In comparison, the encapsulated *Moringa* nanoparticles were more monodisperse, with an average diameter of 222 nm, a polydispersity of 0.2, and diverse sizes (See FIG. 2 and Table 2).

TABLE 1

Zetasizer results for *Moringa* nanopartieles

|  |  |  | Size (d.nm) | % Intensity | St Dev (d.nm) |
|---|---|---|---|---|---|
| Z-Avg (d.nm) | 141.0 | Peak 1 | 145.8 | 94.9 | 57.33 |
| PDI | 0.324 | Peak 2 | 19.82 | 5.1 | 4.006 |
| Intercept | 0.910 | Peak 3 | 0.000 | 0.0 | 0.000 |

TABLE 2

Zetasizer results for encapsulated *Moringa* nanoparticles

|  |  |  | Size (d.m) | % Intensity | St Dev (d.nm) |
|---|---|---|---|---|---|
| Z-Avg (d.nm) | 222.0 | Peak 1 | 231.0 | 95.3 | 94.30 |
| PDI | 0.282 | Peak 2 | 4970 | 4.7 | 626.2 |
| Intercept | 0.952 | Peak 3 | 0.000 | 0.0 | 0.000 |

Figure 3:
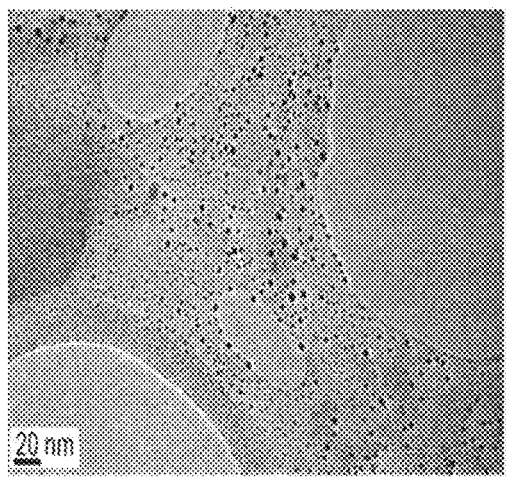
FIG. 3 depicts a transmission electron micrograph of *Moringa oleifera* nanoparticles.
Figure 4:
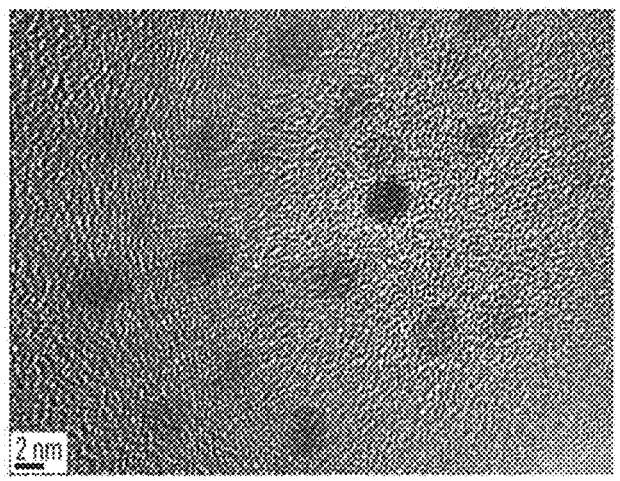
FIG. 4 depicts a transmission electron micrograph of *Moringa oleifera* nanoparticles.
Figure 5:
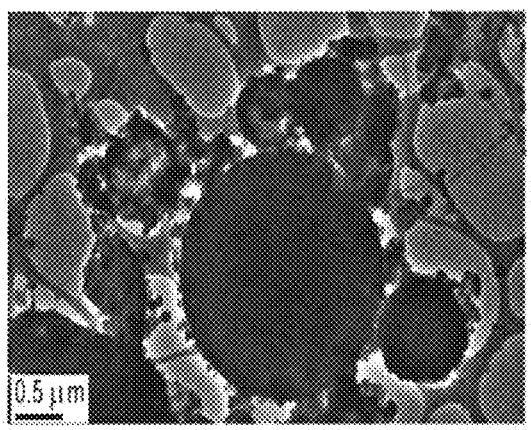
FIG. 5 depicts a transmission electron micrograph of encapsulated *Moringa oleifera* nanoparticles.
Figure 6:
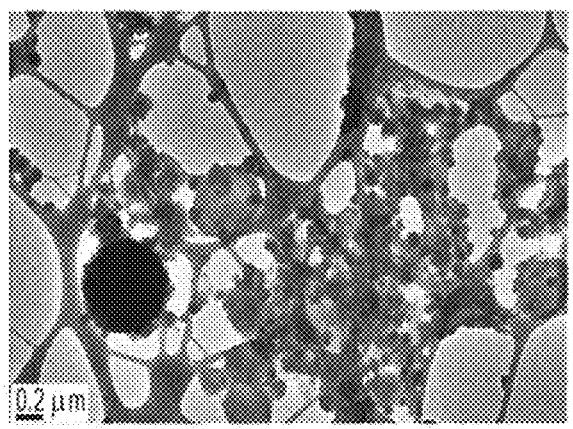
FIG. 6 depicts a transmission electron micrograph of encapsulated *Moringa oleifera* nanoparticles.
Figure 7:
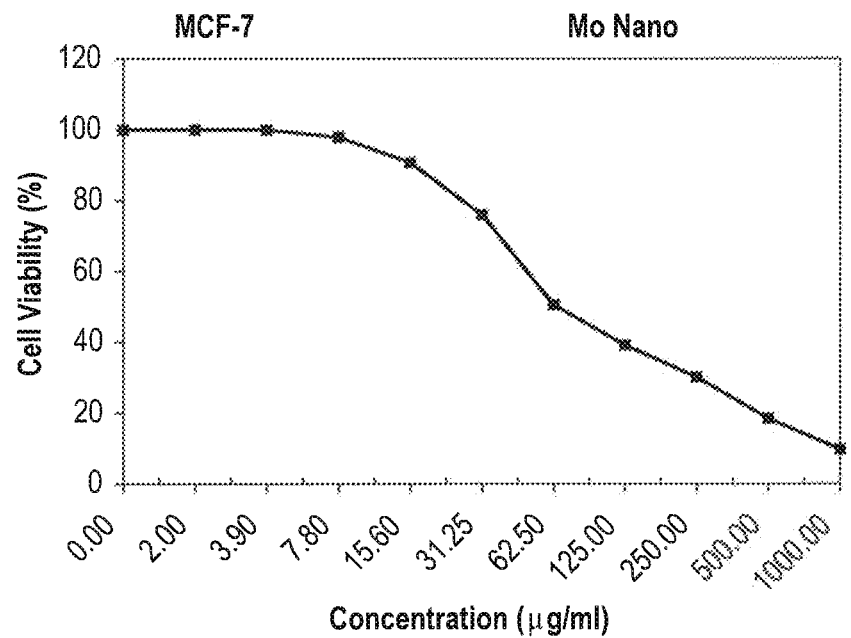
FIG. 7 depicts a graph of the cytotoxicity of *Moringa oleifera* nanoparticles against MCF-7 cells.
Figure 8:
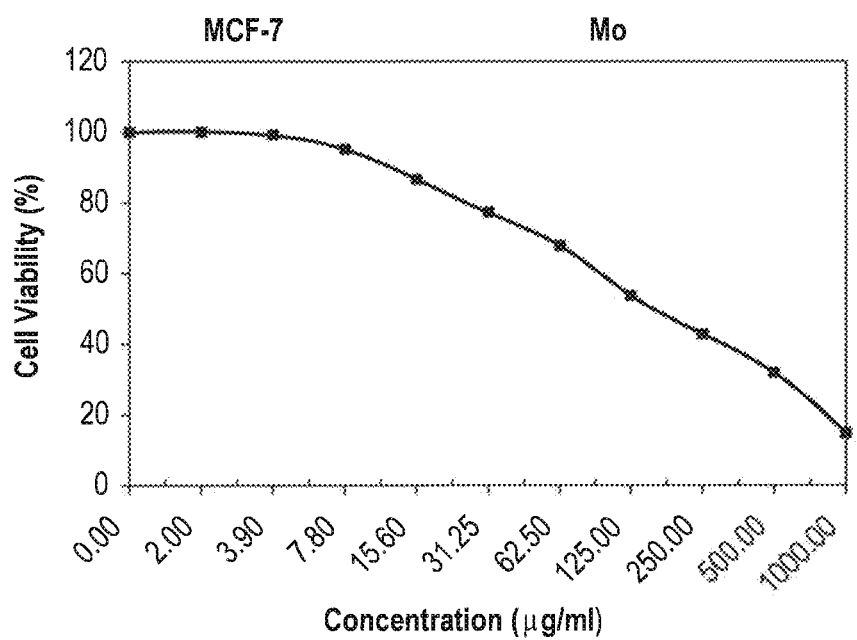
FIG. 8 depicts a graph of the cytotoxicity of powdered *Moringa oleifera* leaves against MCF-7 cells.
Figure 9:
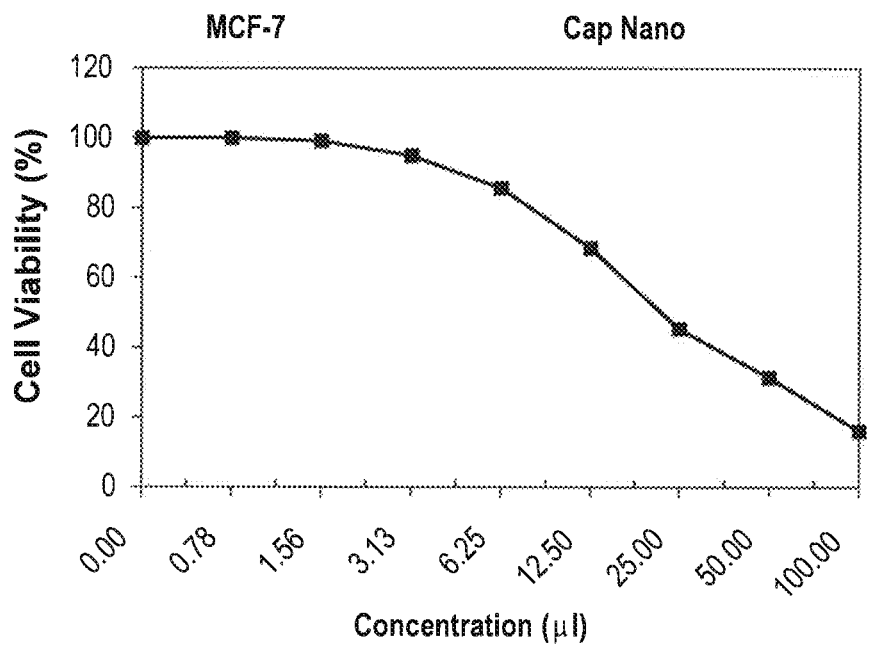
FIG. 9 depicts a graph of the cytotoxicity of encapsulated *Moringa oleifera* nanoparticles against MCF-7 cells.
Figure 10:
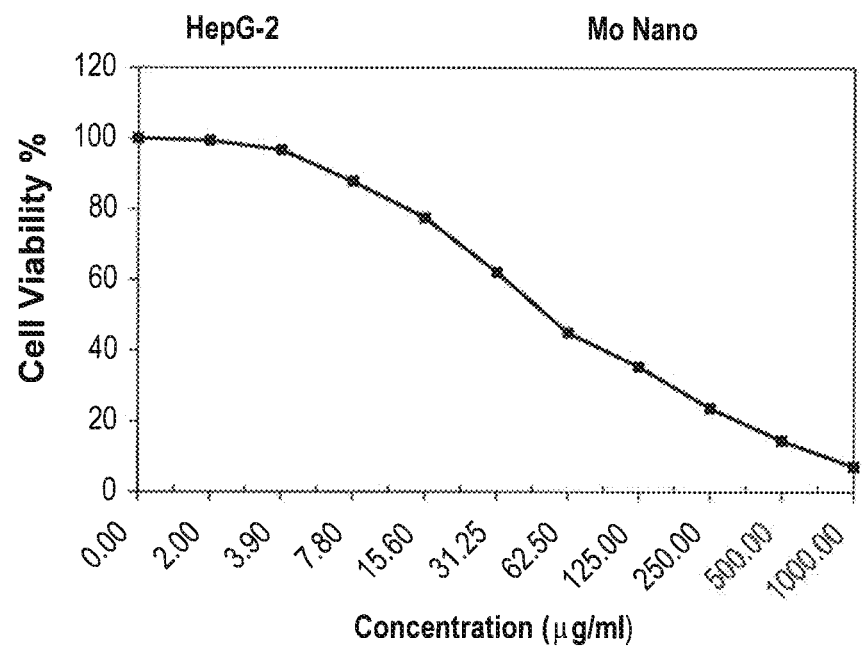
FIG. 10 depicts a graph of the cytotoxicity of *Moringa oleifera* nanoparticles against HepG-2 cells.
Figure 11:
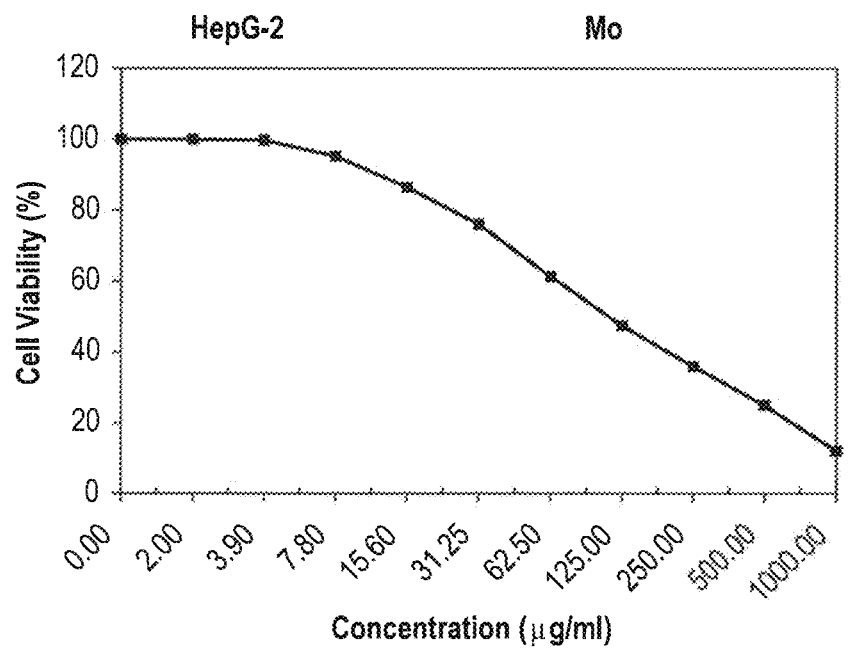
FIG. 11 depicts a graph of the cytotoxicity of powdered *Moringa oleifera* leaves against HepG-2 cells.
Figure 12:
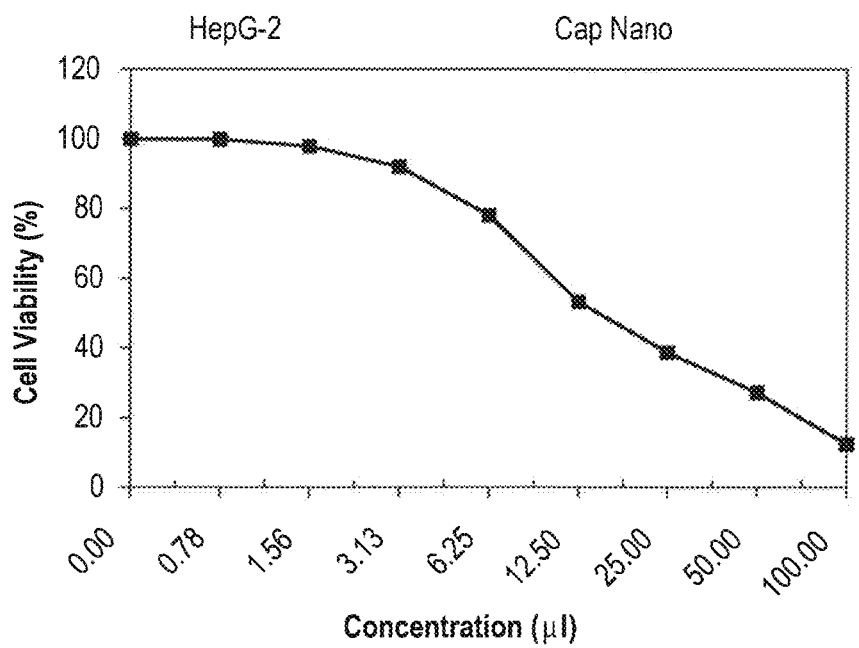
FIG. 12 depicts a graph of the cytotoxicity of encapsulated *Moringa oleifera* nanoparticles against HepG-2 cells.

Transmission electron microscopy (TEM) was performed using a JEM-1011 (JEOL, Japan), to study the surface morphology, shape, and size of the *Moringa* nanoparticles. As shown in FIGS. 3 and 4, the *Moringa* nanoparticles are spherical in shape with diverse sizes. As shown in FIGS. 5 and 6, the encapsulated *Moringa* nanoparticles are encapsulated and covered by a polymer layer.

Example 4

Evaluation of the Cytotoxic Effects of *Moringa* Nanoparticles Against Cancer Cells Mammalian MCF-7 cells (a human breast cancer cell line) and HepG-2 cells (a human liver cancer cell line) were obtained from the VACSERA Tissue Culture Unit. Dimethyl sulfoxide (DMSO), crystal violet, and trypan blue dye were purchased from Sigma (St. Louis, Mo., USA). Fetal Bovine Serum (FBS), Dulbecco's modified Eagle's medium (DMEM), RPMI-1640, HEPES buffer solution, L-glutamine, gentamycin and 0.25% Trypsin-EDTA were purchased from Lonza. Crystal violet stain (1%) was prepared by mixing 0.5% (w/v) crystal violet and 50% methanol, brought up to volume with ddH$_2$O and filtered through Whatman No. 1 filter paper.

MCF-7 and HepG-2 cell lines were propagated in DMEM supplemented with 10% heat-inactivated FBS, 1% L-glutamine, HEPES buffer and 50 µg/ml gentamycin. All cells were maintained at 37° C. in a humidified atmosphere with 5% CO$_2$ and were sub-cultured two times a week.

Cytotoxicity assays were performed by seeding cells from each cell line into 96-well flat-bottomed microtiter plates (Falcon, N.J., USA) at a concentration of 1×10$^4$ cells per well in 100 µl of growth medium. Fresh medium containing different concentrations of the test sample was added after 24 hours of incubation. Specifically, serial two-fold dilutions of each sample to be tested were added to the confluent cell monolayers using a multichannel pipette. The microtiter plates were then incubated at 37° C. in a humidified incubator with 5% CO$_2$ for a period of 48 hours. Three wells were used for each concentration of the tested samples. Control cells were incubated without adding any of the tested samples, and with or without the addition of DMSO. The percentage of DMSO present in the wells (a maximum of 0.1%) was found not to affect the experiment. After the incubation period, the respective concentrations of the sample used for each well were added to the wells once again, and the incubation was continued for a further 24 hours. Viable cells were then counted by a colorimetric method.

Briefly, media was aspirated from each well and crystal violet solution (1%) was added for at least 30 minutes. The stain was then removed and the plates were rinsed with tap water to remove all excess stain. Glacial acetic acid (30%) was then added to the wells and mixed thoroughly and the absorbance was measured after gentle shaking using a Microplate reader (Tecan, Inc.) at a wavelength of 490 nm. The results were corrected for background absorbance detected in control wells without any added stain. Treated samples were then compared with stained control wells. All experiments were carried out in triplicate. The cytotoxic effect of each tested composition was calculated. Briefly, the optical density of each well was measured with a microplate reader (SunRise, Tecan, Inc., USA) to determine the number of viable cells and the percentage of viability was calculated according to Equation 1:

$$\left[\frac{OD_t}{OD_c}\right] \times 100\%$$

In Equation 1, OD$_t$ is the mean optical density of wells treated with a particular test sample and OD$_c$ is the mean optical density of untreated (control) cells. The relation between surviving cells and test sample concentration is plotted to reveal the survival curve of each tumor cell line after treatment with a particular composition. The 50% inhibitory concentration (IC$_{50}$), the concentration required to cause toxic effects in 50% of intact cells, was then estimated from the graphic plots of the dose response curve using Graphpad Prism software (San Diego, Calif., USA).

As illustrated in FIGS. 7-12, a significant decrease in cell survival was observed in both MCF-7 and HepG-2 cancer cell lines when treated with *Moringa* leaf powder, *Moringa* nanoparticles, and encapsulated *Moringa* nanoparticles. For MCF-7, an IC$_{50}$ of 168±27.04 µg/ml was observed for *Moringa* leaf powder (M$_o$). (See Table 4). The inhibitory activity of *Moringa* nanoparticles (MoN) was significantly enhanced when compared to *Moringa* leaf powder alone, with an IC$_{50}$ of 65.6±13.97 µg/ml. (See Table 3). This inhibitory activity was further enhanced for the encapsulated *Moringa* nanoparticles (Mo CapN), with an IC$_{50}$ of 22.5±0.63 µg/100 µl. (See Table 5) For HepG-2, an IC$_{50}$ of 113.5±6.59 µg/ml was observed for *Moringa* leaf powder (M$_o$). The inhibitory activity of *Moringa* nanoparticles (MoN) was significantly enhanced when compared to *Moringa* leaf powder alone, with an IC$_{50}$ of 53.4±1.93 µg/ml. (See Tables 6 and 7). This inhibitory activity was further enhanced for the encapsulated *Moringa* nanoparticles (Mo CapN), with an IC$_{50}$ of 15.2±2.37 µg/100 µl. (See Table 8). Thus, encapsulating the *Moringa* nanoparticles resulted in a significantly enhanced inhibitory activity against both MCF-7 and HepG-2 cancer cell lines.

TABLE 3

Inhibitory Activity of Moringa Nanoparticles against MCF-7 (Breast Cancer) Cells (IC$_{50}$ = 65.5 ± 13.97 µg/ml)

| Conc. (µg/ml) | Viability % (Replicates) | | | | Inhibitory | |
|---|---|---|---|---|---|---|
| | 1$^{st}$ | 2$^{nd}$ | 3$^{rd}$ | Mean | % | S.D. ± |
| 1000 | 9.75 | 10.86 | 8.61 | 9.74 | 90.26 | 1.13 |
| 500 | 17.43 | 19.94 | 18.02 | 18.46 | 81.54 | 1.31 |
| 250 | 26.81 | 39.75 | 30.89 | 30.15 | 69.85 | 3.04 |
| 125 | 35.24 | 40.88 | 41.67 | 39.26 | 60.74 | 3.51 |
| 62.5 | 48.7 | 48.7 | 54.26 | 50.55 | 49.45 | 3.21 |
| 31.25 | 73.28 | 19.81 | 74.92 | 76.00 | 24.00 | 3.40 |
| 15.6 | 89.06 | 94.13 | 89.06 | 90.75 | 9.25 | 2.93 |
| 7.8 | 97.84 | 99.52 | 96.41 | 97.92 | 2.08 | 1.56 |
| 3.9 | 100 | 100 | 99.87 | 99.96 | 0.04 | 0.08 |
| 2 | 100 | 100 | 100 | 100 | 0.00 | 0.00 |
| 0 | 100 | 100 | 100 | 100 | 0.00 | |

TABLE 4

Inhibitory Activity of Moringa Leaf Powder against MCF-7 (Breast Cancer) Cells (IC$_{50}$ = 168 ± 27.04 µg/ml)

| Conc. (µg/ml) | Viability % (Replicates) | | | | Inhibitory | |
|---|---|---|---|---|---|---|
| | 1$^{st}$ | 2$^{nd}$ | 3$^{rd}$ | Mean | % | S.D. ± |
| 1000 | 16.31 | 14.92 | 13.27 | 14.83 | 85.17 | 1.52 |
| 500 | 34.67 | 31.83 | 29.4 | 31.97 | 68.03 | 2.64 |
| 250 | 42.56 | 45.04 | 40.96 | 42.85 | 57.15 | 2.06 |
| 125 | 53.24 | 57.35 | 50.67 | 53.75 | 46.25 | 3.37 |
| 62.5 | 64.39 | 70.21 | 67.95 | 67.85 | 32.15 | 3.06 |
| 31.25 | 72.16 | 79.48 | 80.23 | 77.29 | 22.71 | 4.46 |
| 15.6 | 85.24 | 87.31 | 87.31 | 86.62 | 13.38 | 1.20 |
| 7.8 | 94.06 | 96.28 | 95.34 | 94.23 | 4.77 | 1.11 |
| 3.9 | 99.71 | 99.71 | 98.26 | 99.23 | 0.77 | 0.84 |
| 7 | 100 | 100 | 100 | 100 | 0.00 | 0.00 |
| 0 | 100 | 100 | 100 | 100 | 0.00 | |

TABLE 5

Inhibitory Activity of Encapsulated Moringa Nanoparticles against MCF-7 (Breast Cancer) Cells ($IC_{50}$ = 22.5 ± 0.63 µg/µl medium)

| Conc. (µg/ml) | Viability % (Replicates) | | | | Inhibitory | |
|---|---|---|---|---|---|---|
| | $1^{st}$ | $2^{nd}$ | $3^{rd}$ | Mean | % | S.D. ± |
| 100 | 14.78 | 16.35 | 17.21 | 16.11 | 83.89 | 1.23 |
| 50 | 30.91 | 28.76 | 34.58 | 31.42 | 68.58 | 2.94 |
| 25 | 43.27 | 46.54 | 46.54 | 45.45 | 54.55 | 1.89 |
| 12.5 | 68.95 | 65.32 | 71.38 | 68.55 | 31.45 | 3.05 |
| 6.25 | 85.2 | 82.78 | 89.04 | 85.67 | 14.33 | 3.16 |
| 3.125 | 94.31 | 93.27 | 97.32 | 94.97 | 5.03 | 2.10 |
| 1.56 | 99.45 | 98.16 | 100 | 99.20 | 0.80 | 0.94 |
| 0.78 | 100 | 100 | 100 | 100 | 0.00 | 0.00 |
| 0 | 100 | 100 | 100 | 100 | 0.00 | |

TABLE 6

Inhibitory Activity of Moringa Nanoparticles against HepG-2 (Liver Cancer) Cells ($IC_{50}$ = 53.4 ± 1.93 µg/ml)

| Conc. (µg/ml) | Viability % (Replicates) | | | | Inhibitory | |
|---|---|---|---|---|---|---|
| | $1^{st}$ | $2^{nd}$ | $3^{rd}$ | Mean | % | S.D. ± |
| 1000 | 6.89 | 8.52 | 5.97 | 7.13 | 92.87 | 1.29 |
| 500 | 14.27 | 17.09 | 12.34 | 14.57 | 85.43 | 2.39 |
| 250 | 20.35 | 26.78 | 24.19 | 23.77 | 76.23 | 1.24 |
| 125 | 31.71 | 35.27 | 39.42 | 35.47 | 64.53 | 3.85 |
| 62.5 | 42.36 | 44.95 | 47.81 | 45.04 | 54.96 | 2.73 |
| 31.25 | 64.88 | 62.37 | 59.2 | 62.15 | 37.85 | 2.85 |
| 15.6 | 78.64 | 79.51 | 74.38 | 77.51 | 22.49 | 2.75 |
| 7.8 | 90.17 | 88.04 | 85.29 | 87.83 | 12.17 | 2.45 |
| 3.9 | 99.74 | 93.38 | 94.03 | 96.72 | 3.28 | 2.87 |
| 2 | 100 | 99.12 | 99.12 | 99.41 | 0.59 | 0.51 |
| 0 | 100 | 100 | 100 | 100 | 0.00 | |

TABLE 7

Inhibitory Activity of Moringa Leaf Powder against HepG-2 (Liver Cancer) Cells ($IC_{50}$ = 113.5 ± 6.59 µg/ml)

| Conc. (µg/ml) | Viability % (Replicates) | | | | Inhibitory | |
|---|---|---|---|---|---|---|
| | $1^{st}$ | $2^{nd}$ | $3^{rd}$ | Mean | % | S.D. ± |
| 1000 | 11.74 | 10.65 | 13.59 | 11.99 | 88.01 | 1.49 |
| 500 | 24.81 | 23.29 | 26.73 | 24.94 | 75.06 | 1.77 |
| 250 | 32.95 | 36.76 | 38.09 | 35.93 | 64.07 | 2.67 |
| 125 | 46.23 | 49.02 | 47.14 | 47.46 | 52.54 | 1.42 |
| 62.5 | 58.17 | 65.29 | 60.36 | 61.27 | 38.73 | 3.65 |
| 11.25 | 71.38 | 80.54 | 76.19 | 76.04 | 23.96 | 4.58 |
| 15.6 | 84.52 | 89.43 | 85.27 | 86.41 | 13.59 | 2.65 |
| 7.8 | 95.46 | 97.28 | 93.14 | 95.29 | 4.71 | 2.08 |
| 3.9 | 99.72 | 100 | 989.72 | 99.81 | 0.19 | 0.16 |
| 2 | 100 | 100 | 100 | 100 | 0.00 | 0.00 |
| 0 | 100 | 100 | 100 | 100 | 0.00 | |

TABLE 8

Inhibitory Activity of Encapsulated Moringa Nanoparticles against HepG-2 (Liver Cancer) Cells ($IC_{50}$ = 15.2 ± 2.37 µg/µl medium)

| Conc. (µg/ml) | Viability % (Replicates) | | | | Inhibitory | |
|---|---|---|---|---|---|---|
| | $1^{st}$ | $2^{nd}$ | $3^{rd}$ | Mean | % | S.D. ± |
| 100 | 12.39 | 10.88 | 13.74 | 12.34 | 87.66 | 1.43 |
| 50 | 25.28 | 26.94 | 29.43 | 27.22 | 72.78 | 2.09 |
| 25 | 36.45 | 38.67 | 41.02 | 38.71 | 61.29 | 2.29 |
| 12.5 | 49.62 | 53.21 | 56.89 | 53.24 | 46.76 | 3.64 |
| 6.25 | 74.24 | 76.98 | 82.95 | 78.06 | 21.94 | 4.45 |
| 3.125 | 89.56 | 91.43 | 95.28 | 92.09 | 7.91 | 2.92 |
| 1.56 | 96.43 | 98.08 | 99.25 | 97.92 | 2.08 | 1.42 |
| 0.78 | 99.62 | 100 | 100 | 99.87 | 0.13 | 0.22 |
| 0 | 100 | 100 | 100 | 100 | 0.00 | |

Example 5

Evaluation of the Antidiabetic Activity of Moringa Nanoparticles

Current treatments of diabetes mainly focus on reducing fluctuations in blood sugar and subsequent complications. α-amylase and α-glucosidase inhibitors are currently used for diabetic treatment as oral hypoglycemic agents. Acarbose is a commercially available enzyme inhibitor for type II diabetes. In the present study, Moringa leaves (Mo) and Moringa nano-formulations, including Moringa nanoparticles (MoN) and encapsulated Moringa nanoparticles (Mo-CapN) were evaluated for their inhibitory effect on α-amylase and α-glucosidase enzymes using in-vitro methods and using Acarbose as a reference anti-diabetic drug.

α-glucosidase (Saccharomyces cerevisiae) and 3,5,di-nitrosalicylicacid (DNS) were purchased from Sigma-Aldrich (Bangalore). P-nitro-phenyl-α-D-glucopyranoside (p-NPG), sodium carbonate ($Na_2CO_3$), sodium dihydrogen phosphate, and di-sodium hydrogen phosphate were purchased from Hi-Media (Mumbai).

The α-glucosidase and α-amylase inhibitory activity of Moringa leaf powder and Moringa nanoparticles was tested, using Acarbose as a reference drug. Briefly, α-glucosidase inhibitory activity was determined according to standard methods with minor modifications (Shai, L. J. et al., "Inhibitory effects of five medicinal plants on rat alpha-glucosidase: Comparison with their effects on yeast alpha-glucosidase," J. Med. Plant Res. 5: pp. 2863-2867 (2011)). In a 96-well plate, a reaction mixture containing 50 µl phosphate buffer (100 mM, pH=6.8), 10 µl alpha-glucosidase (1 U/ml), and 20 µl of varying concentrations of each tested composition (1000 to 7.81 µg/ml) was preincubated at 37° C. for 15 minutes. Then, 20 µl P-NPG (5 mM) was added as a substrate and incubated for a further 20 minutes at 37° C. The reaction was stopped by adding 50 µl $Na_2CO_3$ (0.1 M). The absorbance of the released p-nitrophenol was measured at 405 nm using a Multiplate Reader. Acarbose at various concentrations (1000 to 7.81 µg/ml) was included as a standard. Control wells were maintained without adding any of the tested compositions. Each experiment was performed in triplicate. The results are expressed as percent inhibition, which was calculated using Formula 2:

$$\text{Inhibitory Activity \%} = \left(1 - \frac{A_s}{A_c}\right) \times 100$$

Wherein $A_s$ is the absorbance of the tested composition and $A_c$ is the absorbance of the control samples. Results are expressed in terms of mean standard deviation and $IC_{50}$ values were calculated using GraphPad.

The α-amylase inhibitory activity of the *Moringa* leaf powder and the *Moringa* nanoparticles was also tested as previously described. Briefly, a volume of 150 µl of each composition to be tested or of the standard drug (acarbose) at concentrations varying from 2000-7.81 µg/ml was incubated with 50 µl of porcine pancreatic amylase (2 U/ml) in phosphate buffer (100 mM, pH 6.8) at 37° C. for 20 minutes in a 96-well plate. Then 100 µl of 1% starch dissolved in 100 mM phosphate buffer (pH 6.8) was further added to the reaction mixture and incubated at 37° C. for 1 hour. Dinitrosalicylate colour reagent (1 ml) was then added and boiled for 10 minutes. The absorbance of the resulting mixture was read at 540 nm and the inhibitory activity was again calculated according to Formula 2 above. All measurements were performed in triplicate and results are expressed in terms of mean±standard deviation and $IC_{50}$ values were calculated using GraphPad.

Figure 16:
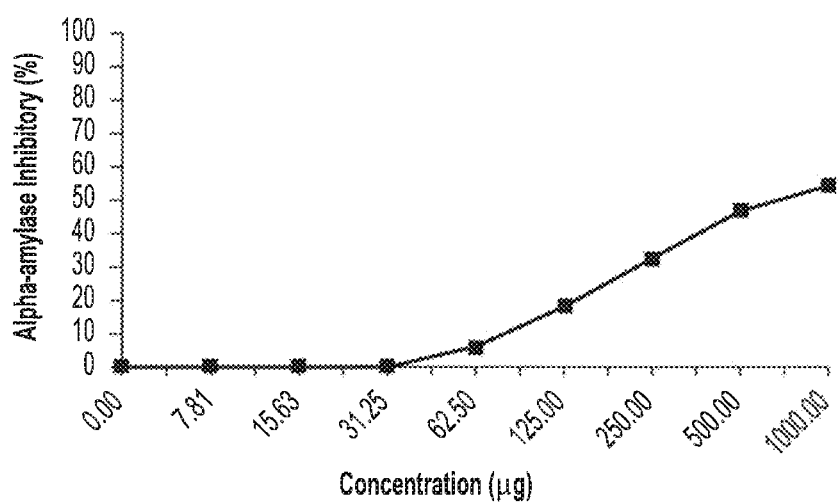
FIG. 16 depicts a graph of the anti-alpha-amylase inhibitory activity of *Moringa oleifera* nanoparticles.
Figure 17:
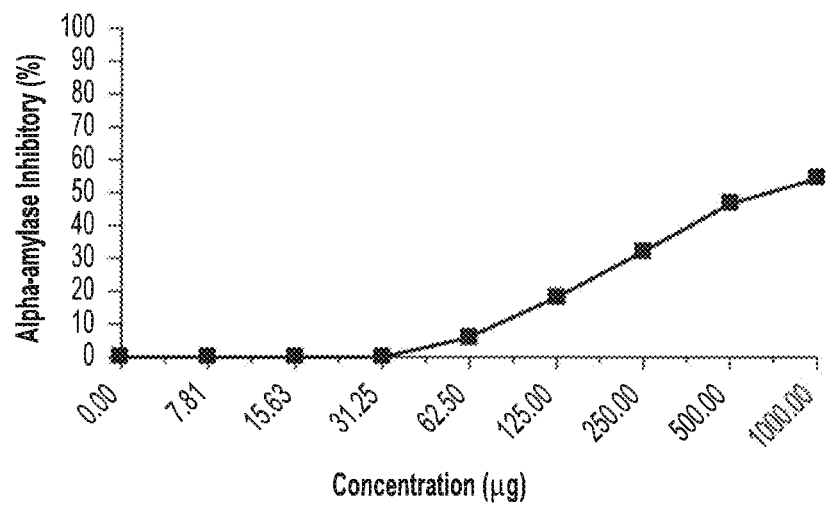
FIG. 17 depicts a graph of the anti-alpha-amylase inhibitory activity of powdered *Moringa oleifera* leaves.
Figure 18:
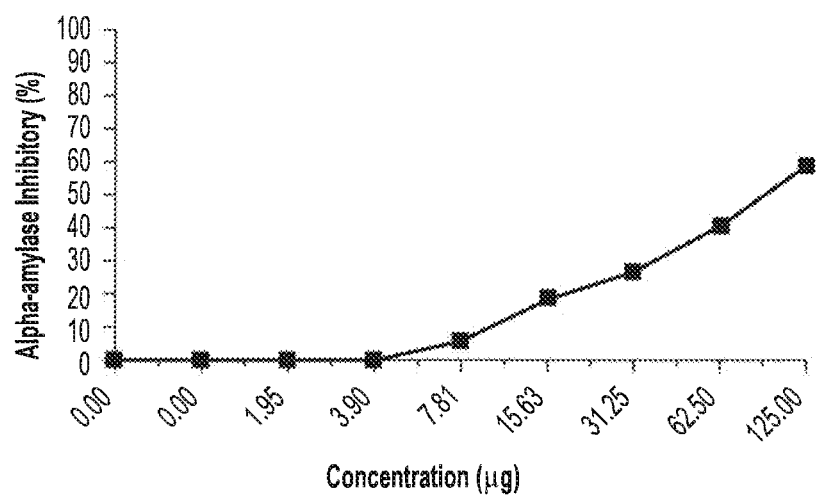
FIG. 18 depicts a graph of the anti-alpha-amylase inhibitory activity of encapsulated *Moringa oleifera* nanoparticles.

The inhibitory potency of *Moringa* leaves against α-amylase activity resulted in an $IC_{50}$ value of 719.92±4.41 µg. (See Table 9 and FIG. 17). In comparison, the nano-formulations were significantly more efficacious as is evident from the $IC_{50}$ values of 15.9±1.11 µg (MoN) and 94.02±1.50 µg (MoCapN). (See Tables 10 and 11 and FIGS. 16 and 18).

Figure 13:
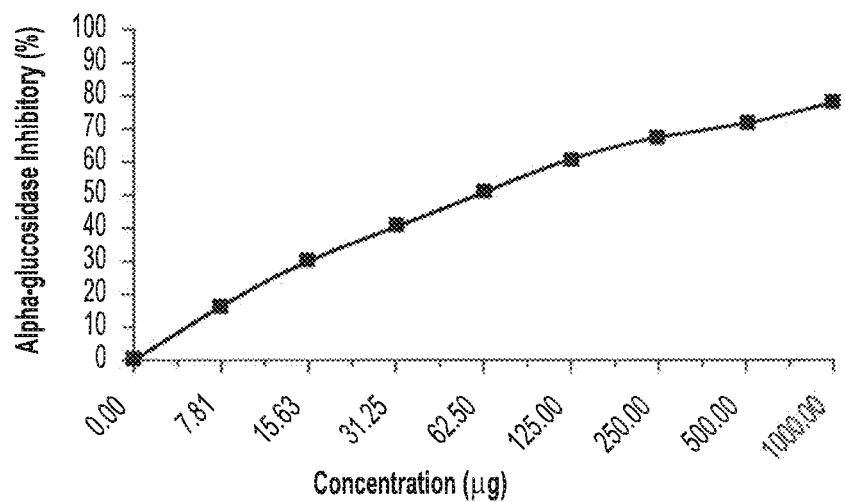
FIG. 13 depicts a graph of the anti-alpha-glucosidase inhibitory activity of *Moringa oleifera* nanoparticles.
Figure 14:
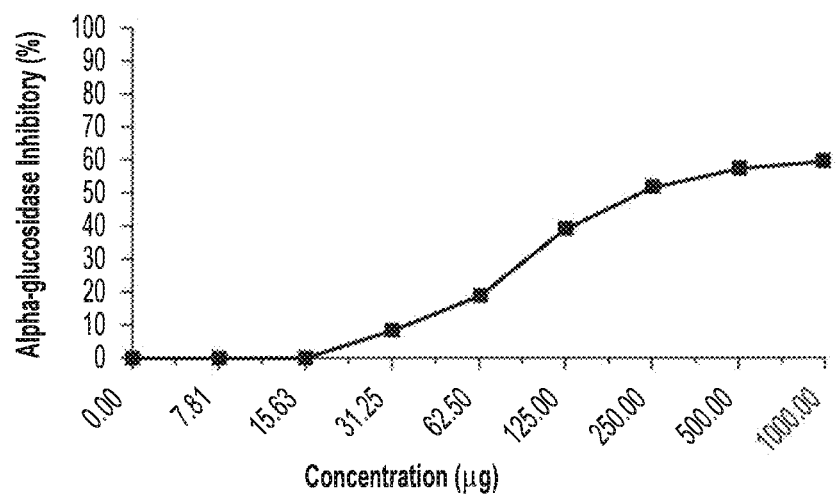
FIG. 14 depicts a graph of the anti-alpha-glucosidase inhibitory activity of powdered *Moringa oleifera* leaves.
Figure 15:
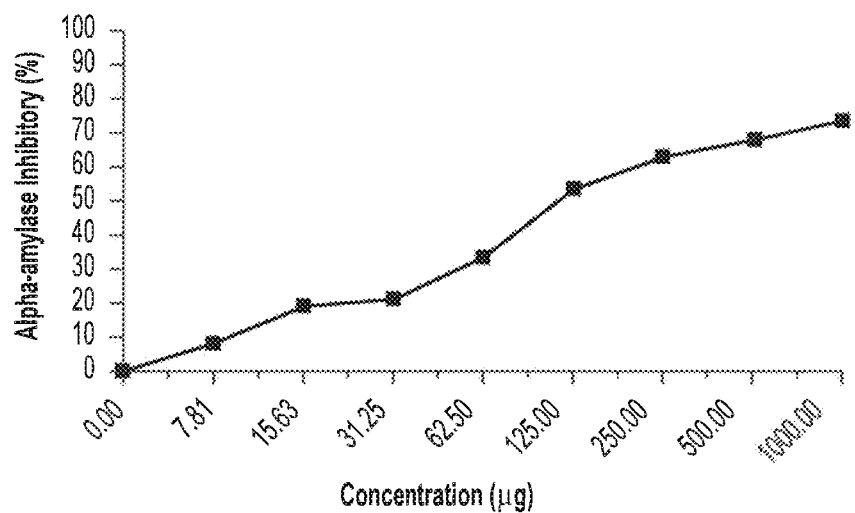
FIG. 15 depicts a graph of the anti-alpha-glucosidase inhibitory activity of encapsulated *Moringa oleifera* nanoparticles.

Further, the inhibitory potency of *Moringa* leaves against α-glucosidase activity demonstrated an $IC_{50}$ value of 231.08±3.73 µg/m. (See Table 12 and FIG. 14). In comparison, the nano-formulations were significantly more efficacious as is evident from their $IC_{50}$ values of 59.38±1.42 (MoN) and 30.13±0.83 µg (MoCapN). (See Tables 13 and 14 and FIGS. 13 and 15).

TABLE 9

Anti-α-amylase Activity of *Moringa* Leaves

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 1,000 | 54.41 | 53.68 | 54.84 | 54.31 | 0.59 |
| 500 | 46.38 | 47.12 | 46.36 | 46.62 | 0.43 |
| 250 | 31.24 | 32.46 | 31.84 | 31.85 | 0.61 |
| 125 | 17.63 | 17.24 | 18.94 | 17.94 | 0.89 |
| 62.5 | 6.35 | 5.84 | 5.98 | 6.06 | 0.26 |
| 31.25 | 0 | 0 | 0 | 0.00 | 0.00 |
| 15.63 | 0 | 0 | 0 | 0.00 | 0 |
| 7.81 | 0 | 0 | 0 | 0.00 | 0 |
| 0 | 0 | 0 | 0 | 0.00 | 0 |
| $IC_{50}$ | 725.40 | 719.5 | 714.62 | 719.72 | 4.41 |

TABLE 10

Anti-α-amylase Activity of *Moringa* Nanoparticles

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 1,000 | 74.35 | 72.16 | 72.79 | 73.10 | 1.13 |
| 500 | 68.39 | 68.14 | 66.39 | 67.64 | 1.09 |
| 250 | 62.31 | 64.32 | 62.31 | 62.98 | 1.16 |
| 125 | 52.14 | 53.46 | 52.98 | 52.86 | 0.67 |
| 62.5 | 34.28 | 32.16 | 32.96 | 33.13 | 1.07 |
| 31.25 | 21.32 | 20.68 | 20.34 | 20.78 | 0.50 |
| 15.63 | 19.32 | 18.34 | 18.11 | 18.59 | 0 |
| 7.81 | 8.39 | 6.99 | 7.68 | 7.66 | 0 |
| 0 | 0 | 0 | 0 | 0.00 | 0 |
| $IC_{50}$ | 117.51 | 114.8 | 115.69 | 115.9 | 1.11 |

TABLE 11

Anti-α-amylase Activity of Encapsulated *Moringa* Nanoparticles

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 195 | 59.37 | 58.31 | 59.06 | 58.91 | 0.55 |
| 62.5 | 41.08 | 40.31 | 41.39 | 40.93 | 0.56 |
| 31.25 | 26.31 | 27.81 | 27.33 | 27.15 | 0.77 |
| 15.63 | 19.42 | 17.98 | 19.25 | 18.88 | 0.67 |
| 7.81 | 6.35 | 5.91 | 6.22 | 6.16 | 0 |
| 3.9 | 0 | 0 | 0 | 0.00 | 0 |
| 1.95 | 0 | 0 | 0 | 0.00 | 0 |
| 0.98 | 0 | 0 | 0 | 0.00 | 0 |
| 0 | 0 | 0 | 0 | 0.00 | 0 |
| $IC_{50}$ | 92.98 | 96.14 | 92.95 | 94.0.2 | 1.50 |

TABLE 12

Anti-α-glucosidase Activity of *Moringa* Leaves

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 1,000 | 60.34 | 61.32 | 58.41 | 60.02 | 1.48 |
| 500 | 59.31 | 57.11 | 55.71 | 57.44 | 1.80 |
| 250 | 51.24 | 51.32 | 50.92 | 51.16 | 1.24 |
| 125 | 39.84 | 40.13 | 39.25 | 39.74 | 0.45 |
| 62.5 | 19.68 | 19.14 | 18.32 | 19.05 | 0.68 |
| 31.25 | 9.35 | 7.31 | 7.89 | 8.18 | 1.05 |
| 15.63 | 0 | 0 | 0 | 0.00 | 0 |
| 7.81 | 0 | 0 | 0 | 0.00 | 0 |
| 0 | 0 | 0 | 0 | 0.00 | 0 |
| $IC_{50}$ | 236.4035 | 235.2547 | 240.1457 | 231.079 | 3.73 |

TABLE 13

Anti-α-glucosidase Activity of *Moringa* Nanoparticles

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 1,000 | 78.31 | 78.91 | 76.31 | 77.84 | 1.36 |
| 500 | 71.39 | 72.55 | 70.37 | 71.44 | 1.09 |
| 250 | 67.14 | 68.55 | 66.31 | 67.26 | 1.02 |
| 125 | 62.17 | 60.17 | 60.17 | 60.84 | 1.15 |
| 62.5 | 51.42 | 50.32 | 51.31 | 51.02 | 0.61 |
| 31.25 | 41.67 | 41.55 | 39.22 | 40.81 | 1.38 |
| 15.63 | 29.44 | 30.66 | 31.28 | 30.46 | 0 |
| 7.81 | 16.71 | 17.18 | 16.34 | 16.74 | 0 |
| 0 | 0 | 0 | 0 | 0.00 | 0 |
| $IC_{50}$ | 57.94872 | 61.35975 | 59.11394 | 59.378 | 1.42 |

TABLE 14

Anti-α-glucosidase Activity of Encapsulated *Moringa* Nanoparticles

| Conc. (µg/ml) | Inhibitory activity (Replicates) | | | Mean | S.D. ± |
|---|---|---|---|---|---|
| | $1^{st}$ | $2^{nd}$ | $3^{rd}$ | | |
| 125 | 76.34 | 77.11 | 74.32 | 75.99 | 1.53 |
| 62.5 | 62.15 | 66.17 | 63.24 | 63.85 | 2.08 |
| 31.25 | 51.37 | 54.71 | 50.68 | 52.25 | 2.16 |

TABLE 14-continued

Anti-α-glucosidase Activity of Encapsulated *Moringa* Nanoparticles

| Conc. (μg/ml) | Inhibitory activity (Replicates) | | | Mean | S.D. ± |
|---|---|---|---|---|---|
| | $1^{st}$ | $2^{nd}$ | $3^{rd}$ | | |
| 15.63 | 20.34 | 22.14 | 21.24 | 21.24 | 0.90 |
| 7.81 | 12.24 | 12.16 | 12.89 | 12.43 | 0.40 |
| 3.9 | 8.36 | 7.84 | 8.67 | 8.29 | 0.42 |
| 1.95 | 0 | 0 | 0 | 0.00 | 0 |
| 0.98 | 0 | 0 | 0 | 0.00 | 0 |
| 0 | 0 | 0 | 0 | 0.00 | 0 |
| $IC_{50}$ | 30.57 | 28.99 | 30.89 | 30.13 | 0.83 |

It can be concluded that, *Moringa* leaves and *Moringa* nano-formulations exhibited potent anti-cancer and anti-diabetic activities, with the *Moringa* nano-formulations being more effective anti-cancer agents and anti-diabetic agents, and with the encapsulated *Moringa* nanoparticles being even more effective than the *Moringa* nanoparticles alone. This could be attributed to an enhanced bioavailability of the phytochemical constituents of *Moringa* leaves in the nano-formulations, allowing for synergistic effects of these phytochemical constituents.

It is to be understood that the encapsulated *Moringa oleifera* nanoparticles are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Moringa* nanoparticles, comprising:
   harvesting the *Moringa oleifera* leaves only from a *Moringa oleifera* tree;
   drying only the harvested *Moringa oleifera* leaves; and
   powdering the *Moringa oleifera* leaves to form the powdered *Moringa oleifera* leaves mixing the powdered *Moringa oleifera* leaves with a solvent to form a solution;
   spraying the solution dropwise into boiling water under ultrasonic conditions to form a mixture;
   stirring the resulting mixture to form the *Moringa* nanoparticles, wherein the nanoparticles have an average particle diameter of about 222 nm with a polydispersity of about 0.2; and
   encapsulating the *Moringa* nanoparticles in a mixture comprising gum olibanum and polyvinyl alcohol, wherein the ratio of *Moringa* nanoparticles:gum olibanum:polyvinyl alcohol is 1:5:7 (w/w/w).

2. The method of claim 1, wherein the leaves are obtained from a *Moringa oleifera* tree grown in Riyadh, Saudi Arabia.

3. The method of claim 1, wherein:
   400 mg of the powdered *Moringa oleifera* leaves are mixed with 20 ml of the solvent;
   the solution is sprayed dropwise into 50 ml of boiling water at a flow rate of 0.2 ml/min for 5 minutes; and
   the resulting mixture is stirred at about 200-800 rpm at room temperature for about 20 minutes to form the *Moringa* nanoparticles.

* * * * *